United States Patent [19]

Slack et al.

[11] Patent Number: 5,349,082
[45] Date of Patent: Sep. 20, 1994

[54] TOLUENE DIISOCYANATE RESIDUE

[75] Inventors: William E. Slack, Moundsville; Kenneth L. Dunlap, New Martinsville, both of W. Va.; Larry W. Arndt, Pasadena, Tex.; Louis Renbaum, Richmond Hill, Ga.

[73] Assignee: Miles Inc., Pittsburgh, Pa.

[21] Appl. No.: 33,935

[22] Filed: Mar. 19, 1993

[51] Int. Cl.$^5$ ............................................. C07C 263/20
[52] U.S. Cl. ..................................... 560/352; 560/351
[58] Field of Search ............................... 560/351, 352

[56] References Cited

U.S. PATENT DOCUMENTS

| | | | |
|---|---|---|---|
| 3,128,310 | 4/1964 | Koch | 260/582 |
| 3,331,876 | 7/1967 | Van Horn et al. | 260/582 |
| 3,455,836 | 7/1969 | Shultz et al. | 252/182 |
| 4,168,270 | 9/1979 | Himmele et al. | 260/340 |
| 4,289,589 | 9/1981 | Koehler et al. | 203/49 |
| 4,311,800 | 1/1982 | Reischl | 521/109 |
| 4,910,333 | 3/1990 | Slack | 560/351 |
| 5,198,522 | 3/1993 | Steppan et al. | 528/61 |

FOREIGN PATENT DOCUMENTS 257827  6/1988  Fed. Rep. of Germany.

*Primary Examiner*—José G. Dees
*Assistant Examiner*—Samuel Barts
*Attorney, Agent, or Firm*—Joseph C. Gil; Lyndanne M. Whalen; Godfried R. Akorli

[57] ABSTRACT

Disclosed herein is a process for recovering toluene diisocyanate (TDI) from a TDI residue solution, comprising mixing the residue solution with a polyisocyanate consisting essentially of methylenediphenyl diisocyanate (MDI) or MDI in combination with its higher ring oligomer, followed by heating the resulting mixture over a temperature range of 130° to 250° C. for a period of time sufficient to remove free TDI and thermally splittable TDI generated from equilibration of the TDI residue with MDI or the MDI oligomer by either a batch or continuous process.

5 Claims, No Drawings

TOLUENE DIISOCYANATE RESIDUE

BACKGROUND OF THE INVENTION

1. Field of the Invention

The present invention relates to the process for recovering toluene diisocyanate (TDI) monomers from TDI residues, and the process for preparing new stable polyisocyanate materials by the mixing the TDI residues with MDI and/or MDI oligomers followed by removing the TDI monomers.

2. Brief Description of the Prior Art

It is well known in the art that distillation residues of toluene diisocyanates from the phosgenation products thereof are difficult to handle. During the phosgenation of toluene diamine to toluene diisocyanate followed by distillation of TDI, there are formed relatively high molecular weight by-products containing uretdione, isocyanurate, carbodiimide, uretone imine, urea and/or biuret groups. Depending upon the content of o-toluene diamine starting material, there can also be formed methylbenzimidazoles during phosgenation and with time, they are biuretized with the free isocyanate groups present, with an accompanying formation of cross-linked products. Much work has been done in the art to improve on the process of treating toluene diisocyanate residues in order to make them more useful.

One of the art-known processes for treating toluene diisocyanate residues comprises recycling of the toluene diisocyanate residues and hydrolyzing the residues. Only small amounts of the toluene diisocyanate are converted to toluene diamine. See U.S. Pat. Nos. 3,128,310, 3,331,876 and 4,311,800.

Another proposed process comprises dissolving toluene diisocyanate residues which still have a considerable content of free isocyanate groups (greater than 20% by weight) in an organic solvent in the presence of monomeric diisocyanates, optionally at a high temperature, and for using these residue solutions as the isocyanate component in the polyisocyanate addition process. In practice, however, this process fails because of the inadequate stability of the solution during storage and inability to standardize the solution. See U.S. Pat. Nos. 3,364,361 and 3,455,836.

Yet another process for toluene diisocyanate recovery comprises processing the residue in a fluidized bed at 140 to 280 degrees Centigrade. The remaining residue is of a dust-like consistency and, as such, cannot be further utilized. See DE-OS 2,915,830 and DD-PS 130,142 or DE-OS 2,452,804.

A somewhat related process has been proposed for recovery of the isocyanate components from the toluene diisocyanate residue by introducing other polyisocyanates such as methylene diphenyl diisocyanate into the residue and subsequently distilling the resulting product, and optionally post-treating the resulting product. See DD-257,827-A1 which describes a process by which the distillation residue from toluene diisocyanate production is distilled after mixing with diphenyl methane diisocyanate or its higher ring homologs. Toluene diisocyanate is recovered as a distillate and the sump product is also recovered as an additional isocyanate component. Also see application Ser. No. 07/928,561 filed on Aug. 11, 1992.

The present invention provides an improved process for the recovery of toluene diisocyanate monomer from toluene diisocyanate residue solutions wherein the remaining material is useful as an isocyanate.

SUMMARY OF THE INVENTION

In accordance with the foregoing, the present invention encompasses a process for recovering toluene diisocyanate (TDI) monomer from a TDI residue solution, comprising mixing the residue solution with a polyisocyanate consisting essentially of methylenediphenyl diisocyanate (MDI) or a combination thereof with higher ring oligomers, followed by heating the resulting mixture over a temperature range of 130° to 250° C. at a reduced pressure over a period of time sufficient to remove by, say, distillation both free TDI and thermally splittable TDI monomer generated from equilibration of the TDI residue with MDI and/or MDI oligomers, by either a batch or continuous process.

By the term "TDI residue solution" is meant residue generated from the phosgenation of toluene diamine (TDA) which is dissolved in TDI and/or medium such as solvents, e.g., ortho-dichlorobenzene.

By the term "equilibration" herein is meant the conversion of TDI-based residue to MDI-based residue.

By the term "thermally splittable TDI" is meant TDI monomer that is chemically bound in a polymer matrix which when heated in the presence of MDI will equilibrate to generate TDI monomer.

Also encompassed by the invention is the new stable polyisocyanate material which is prepared by the process of the invention.

It has been found that by the process of this invention, substantially more TDI is recovered from the TDI residue solution than just the free TDI present as the solvent in the residue. It is believed that some of the TDI which is chemically bound in the residue is thermally split and recovered. This and other aspects of the invention are described more fully below.

DETAILED DESCRIPTION OF THE INVENTION

As afore-stated, the toluene diisocyanate residue that is processed in accordance with this invention is a distillation residue that occurs in the preparation of toluene diisocyanate by the reaction of toluene diamine with phosgene (phosgenation) in the presence of a solvent, followed by the distillation of the toluene diisocyanate. In this context, toluene diamine (TDA) defines in particular 2,4-toluene diamine and its commercial mixture with up to 35% by weight (based on the mixture) 2,6-toluene diamine. In addition, up to about 4.5% by weight of a mixture of 2,3- and 3,4-TDA may be present. Correspondingly, toluene diisocyanate (TDI) defines 2,4-toluene diisocyanate and its commercial mixture with up to 35% by weight (based on the mixture) 2,6-toluene diisocyanate.

The toluene diisocyanate residues used in the subject process are typically residues that occur in the production of commercial 2,4-toluene diisocyanate or the commercial mixtures thereof with 20% or 35% 2,6-toluene diisocyanate. These residues generally contain up to 85 weight percent of free and reversibly chemically bound (i.e., thermally splittable) toluene diisocyanate monomer.

The process comprises mixing the TDI residue solution with the polyisocyanate consisting essentially of methylenediphenyl diisocyanate (MDI) modified MDI and/or a combination thereof with its higher ring homologs. In accordance with the invention, typically, the polyisocyanate has an NCO content of 31.0 to 33.6%. The methylenediphenyl diisocyanate or the combination thereof with higher ring homologs can be characterized as having a two ring content from 30–100%. Generally, the methylenediphenyl diisocyanate or MDI with higher ring homologs can be prepared by reacting the corresponding amines with phosgene by techniques which are well known in the art. From about 10 to 90% and preferably 50 to 90% of the polyisocyanate is blended with the toluene diisocyanate residue solution.

The process further comprises treating the mixture under conditions sufficient to remove free and thermally splittable TDI. Free TDI can be removed by evaporating it by means such as heating the reaction mixture at temperatures ranging from 30° to 200° and preferably 100° to 200° Centigrade, at reduced pressure.

The process further comprises treating the mixture under conditions sufficient to split and remove the thermally splittable TDI. Typically, the TDI is split off through equilibration with MDI by holding the mixture at an elevated temperature ranging from 130° to 250° C. and preferably 160° to 200° Centigrade, at a pressure of 1 to 40 Torr and preferably 1 to 20 Torr. It is a distinct feature of the invention that a plug-flow process is used wherein a sequential heat treatment followed by removal of TDI monomer by an evaporation step is repeated several times until there is obtained a stable product that at normal storage temperature does not generate TDI monomer. A further feature of the invention is that the heat treatment step is performed at the shortest residence time relative to the selected temperature which gives a stable product, relative to TDI monomer generation. This results in the lowest possible viscosity. The residence time can be from 5 to 120 minutes and preferably from 10 to 40 minutes at a temperature of 130° to 250° C. and preferably 160° to 220° C. By residence time herein is meant the time the mixture is held at the stated elevated temperature.

After the equilibration is complete, preferably immediately thereafter, the free TDI monomer is recovered from the mixture, by distillation. Typically, TDI monomer is removed from the reaction mixture at an elevated temperature of between 130° and 250° C. over the residence time of 5 to 120 minutes at reduced pressure.

In a preferred embodiment of the invention, the process comprises (a) mixing the TDI residue solution with MDI or MDI with higher ring oligomers, followed by (b) removing free TDI monomer present in the TDI residue solution by, say, evaporating the free TDI, typically at a reduced pressure, followed by (c) holding the resulting mixture at an elevated temperature, typically at reduced pressure, which is sufficient to (i) split substantially all the thermally splittable TDI through equilibration with MDI and/or MDI oligomers, and (ii) remove the TDI generated by the equilibration of TDI residue with MDI followed by (d) optionally repeating the equilibration-evaporation step at reduced pressure until no thermally splittable TDI remains.

In a particularly preferred embodiment of the invention, the process comprises mixing the TDI residue solution with MDI or MDI with higher ring oligomers, followed by removing free TDI monomer present in the TDI residue solution by passing the mixture through an evaporation means such as a wiped thin film evaporator or a flasher at a reduced pressure, followed by heating at 160° to 250° C. for about 1 and 30 minutes, followed by again passing the mixture through a wiped thin film evaporator or a flasher at reduced pressure to remove TDI monomer generated by the equilibration of TDI residue with MDI and/or MDI oligomers, followed by optionally repeating the equilibration-evaporation steps at reduced pressure until no thermally splittable TDI remains.

In accordance with the invention the remaining mixture comprises a polyisocyanate material that can be used in the preparation of isocyanate reaction products. The new polyisocyanate material is stable at 50° C. towards generation of TDI. It is further characterized by its viscosity which can be in the range of 50 to 50,000 MPa.s at 25° C. and preferably 50 to 5000 and NCO content of about 24.0 to 31.0 and preferably 27.0 to 31.0 percent.

The invention is further illustrated but is not intended to be limited by the following examples, in which all parts and percentages are by weight unless otherwise specified.

EXAMPLES

In the examples which follow, the following materials were used:

MDI x/y: where x represents the total of diisocyanate in the isocyanate and where y represents the total 2,2'- and 2,4'-isomers of MDI in the isocyanate. When x is less than 100 the difference is made up with the higher homologs of MDI.

Residue Solution 1: Generated by the phosgenation of TDA containing about 80% 2,4-TDA and 20% 2,6-TDA. The analysis of the residue solution 1 is as follows:

| Component | % by weight |
|---|---|
| 2,6-TDI | 12.9 |
| 2,4-TDI | 53.8 |
| Residue | 33.3 |

Residue Solution 2: Generated by the phosgenation of TDA containing about 80% 2,4-TDA and 20% 2,6-TDA. The analysis of the residue solution 2 is as follows:

| Component | % by weight |
|---|---|
| 2,6-TDI | 7.7 |
| 2,4-TDI | 39.2 |
| Ortho-dichlorobenzene | 1.8 |
| Residue | 51.3 |

Residue Solution 3: Generated by the phosgenation of TDA containing about 77% 2,4-TDA, 19% 2,6-TDA, 1.5% 2,3-TDA and 2.5% 3,4-TDA. The analysis of the residue solution 3 is as follows.

| Component | % by weight |
|---|---|
| TDI | 44.0 |
| Ortho-dichlorobenzene | 42.4 |
| Residue | 13.6 |

EXAMPLE 1

To a 500 ml 3-neck flask equipped with a stirrer, thermometer and a distillation take-off adapter connected to a condenser were added 197 parts of MDI 100/56 and 85 parts of residue solution 2. The stirred mixture was subjected to a 1 mm of Hg pressure and then heated to 200° C. over a 20 minute period, held at 200° C. for 10 minutes then quench cooled to 30° C. 164 parts was distilled over which contained 59 parts 2,4'-MDI, 36 parts 4,4'-MDI, 59 parts 2,4-TDI and 10 parts 2,6-TOI. The 59 parts 2,4-MDI and 36 parts 4,4'-MDI were added back to the reaction mixture to give a product with a 29.9% NCO, a viscosity at 25° C. of 70 MPa.s and a 0.03% TDI monomer content. After 3 months storage at 50° C., there was no increase in the TDI monomer content. 66.5% of the residue in the residue solution 2 was converted to TDI. The TDI in the starting residue solution was 83.6% 2,4-TDI and 16.4% 2,6-TDI, while the TDI generated from the residue was 88% 2,4-TDI and 12% 2,6-TDI.

EXAMPLE 2

To a set up as described in Example 1 were added 325 parts of MDI 58/2 and 81 parts of residue solution 2. The stirred solution was subjected to a 1 mm of Hg pressure and then heated to 200° C. over a 35 minute period, held at 200° C. for 10 minutes then quench cooled to 30° C. 98 parts was distilled over which contained 2 parts 2,4'-MDI, 29 parts 4,4'-MDI, 57 parts 2,4-TDI and 10 parts 2,6-TDI. The 2 parts 2,4'-MDI and 29 parts 4,4'-NDI were added back to the reaction mixture to give a product with a 30.1% NCO, a viscosity at 25° C. of 460 MPa.s and a 0.07% TDI monomer content. 68.8% of the residue in the residue solution 2 was converted to TDI. After 3 months storage at 50° C. there was no increase in the TDI monomer content. The TDI in the starting residue solution was 83.6% 2,4-TDI and 16.4% 2,6-TDI, while the TDI generated from the residue was 86.9% 2,4-TDI and 13.1% 2,6-TDI.

EXAMPLE 3

To a set up as described in Example I were added 310 parts of MDI 58/2 and 133 parts of residue solution 2. The stirred solution was subjected to a 1 mm of Hg pressure and then heated to 200° C. over a 40 minute period, held at 200° C. for 10 minutes then quench cooled to 30° C. 156 parts was distilled over which contained 3 parts 2,4'-NDI, 49 parts 4,4'-MDI, 88 parts 2,4-TDI and 16 parts 2,6-TDI. The 3 parts 2,4-MDI and 49 parts 4,4'-NDI were added back to the reaction mixture to give a product with a 28.2% NCO, a viscosity at 25° C. of 2,460 MPa.s and an 0.03% TDI monomer content. 61.1% of the residue in the residue solution 2 was converted to TDI. After 3 months storage at 50° C., there was no increase in the TDI monomer content. The TDI in the starting residue solution was 83.4% 2,4-TDI and 16.4% 2,6-TDI, while the TDI generated from the residue was 86.1% 2,4-TDI and 13.9% 2,6-TDI.

EXAMPLE 4

To a set up as described in Example 1 were added 350 parts of MDI 44/2 and 150 parts of residue solution 2. The stirred solution was subjected to a 1 mm of Hg pressure and then heated to 200° C. over a 36 minute period, held at 200° C. for 10 minutes and then quench cooled to 30° C., 194 parts was distilled over which contained 4 parts 2,4'-MDI, 77 parts 4,4'-MDI, 96 parts 2,4-TDI and 17 parts 2,6-TDI. The 4 parts 2,4'-MDI and 77 parts 4,4'-MDI were added back to the reaction mixture to give a product with a 28.1% NCO, a viscosity at 25° C. of 13,680 MPa.s and a 0.03% TDI monomer content. 55.4% of the residue in the residue solution 2 was converted to TDI. After 3 months storage at 50° C. there was no increase in the TDI monomer content. The TDI in the starting residue solution was 83.6% 2,4-TDI and 16.4% 2,6-TDI, while the TDI generated from the residue was 87.2% 2,4-TDI and 12.8% 2,6-TDI.

EXAMPLE 5

To a set up as described in Example 1 were added 401 parts of MDI 44/2 and 101 parts of residue solution 2. The stirred solution was subjected to a 1 mm of Hg pressure and then heated to 185° C. over a 60 minute period, held at 185° C. for 15 minutes then quench cooled to 30° C. 181 parts was distilled over which contained 5 parts 2,4'-MDI, 98 parts 4,4'-MDI, 67 parts 2,4'TDI and 11 parts 2,6-TDI. The 5 parts 2,4'-MDI and 98 parts 4,4'-MDI were added back to the reaction mixture to give a product with a 29.2% NCO, a viscosity at 25° C. of 1820 MPa.s and a 0.04% TDI monomer content. 58.3% of the residue in the residue solution 2 was converted to TDI. After 3 months storage at 50° C., there was no increase in the TDI monomer content. The TDI in the starting residue solution was 83.6% 2,4-TDI and 16.4% 2,6-TDI, while the TDI generated from the residue was 89.4% 2,4-TDI and 10.6% 2,6-TDI.

EXAMPLE 6

A 60/40 blend by weight of MDI 44/2 and residue solution 1 was passed through a wiped thin film evaporator heated at 160° C. and at 1 mm Hg pressure to remove TDI monomer. This material was then heated at 180° C. for 10 minutes followed by passing through a wiped thin film evaporator and heated at 160° C. and at 1 mm Hg pressure. This procedure was repeated twice and after each pass through the wiped thin film evaporator, any MDI monomer removed was added back to the reaction mixture. The resulting product had an isocyanate content of 28.5%, a viscosity at 25° C. of 2,710 MPa.s and a TDI monomer content of 0.11%. After 3 months storage at 50° C., there was no increase in the TDI monomer content.

EXAMPLE 7

The same procedure of Example 6 was repeated, except that a 50/50 blend of MDI 44/2 and residue solution 1 was used to give a product having an isocyanate content of 27.5%, a viscosity at 25° C. of 8,600 MPa.s and a TDI monomer content of 0.15%. After 3 months storage at 50° C., there was no increase in the TDI monomer content.

EXAMPLE 8

The same procedure of Example 6 was repeated, except a 70/30 blend of MDI 44/2 and residue solution 1 was used to give a product having an isocyanate content of 28.9%, a viscosity at 25° C. of 1,600 MPa.s and a TDI monomer content of 0.16%. After 3 months storage at 50° C., there was no increase in the TDI monomer content.

EXAMPLE 9

To a 1000 ml 3-neck flask equipped with a stirrer, thermometer and a distillation take-off adapter connected to a condenser were added 320 parts of MDI 100/56 and 408 parts of residue solution 3. The stirred mixture was subjected to a 1 mm of Hg pressure and then heated to 200° C. over a 60 minute period, held at 200° C. for 5 minutes then quench cooled to 60° C. The MDI monomer that was removed with the TDI monomer was added back to the reaction mixture. The resulting product had an isocyanate content of 25.9%, a viscosity at 25° C. of 430 MPa.s and a TDI monomer content of 1.1%.

EXAMPLES OF EQUILIBRATION AT VARIOUS TEMPERATURES

A 60/40 blend by weight of MDI 44/2 and residue solution 1 was passed through a wiped thin film evaporator heated at 160° C. and at 1 mm Hg pressure to remove the TDI monomer present as a solvent in the residue solution 1. This reduced the TDI monomer to about 0.75% based on total free TDI content. This material was then heated at various temperatures with no removal of TDI monomer and the rate of formation of TDI monomer followed.

| 100° C. | | 130° C. | | 200° C. | |
|---|---|---|---|---|---|
| Time at 100° C. (min) | % TDI | Time at 130° C. (min) | % TDI | Time at 200° C. (min) | % TDI |
| 15 | 1.75 | 10 | 3.65 | 2 | 9.48 |
| 30 | 2.23 | 20 | 4.69 | 4 | 9.79 |
| 45 | 2.59 | 30 | 5.37 | 6 | 10.0 |
| 60 | 2.96 | 40 | 5.77 | 8 | 9.95 |
| 75 | 3.23 | 50 | 6.07 | 10 | 9.93 |
| 90 | 3.40 | 60 | 6.27 | 15 | 9.88 |
| 105 | 3.62 | 80 | 6.60 | 20 | 9.82 |
| 120 | 3.76 | 100 | 6.87 | | |
| | | 120 | 7.40 | | |

These examples show that equilibration at 200° C. is very fast while at 100° and 130° C. it is much slower and does not reach equilibration after 2 hours.

Using the same 60/40 blend but not passing through the wiped thin film evaporator, the material was heated at 200° C. and the rate of formation of TDI monomer followed. This showed how the equilibration is affected by the presence of TDI monomer. The blend had a 26.7% TDI monomer content, and if all the residue was converted to TDI, the TDI monomer level would have risen to 40.0%. However, only a modest increase was realized, representing about a 30% conversion of residue to TDI monomer.

| Time at 200° C. (min) | % TDI |
|---|---|
| 2 | 30.7 |
| 4 | 30.6 |
| 6 | 30.6 |
| 8 | 30.7 |
| 10 | 30.6 |
| 15 | 30.8 |
| 20 | 30.6 |

A 70/30 blend, with the TDI monomer content reduced to about 0.75% by passing it through a wiped thin film evaporator, was heated at various temperatures to determine the time required to reach equilibration. The results are listed below. It appears that the 160° C. run would need another 5 minutes to reach equilibration.

| 160° C. | | 180° C. | | 200° C. | |
|---|---|---|---|---|---|
| Time at (minutes) | % TDI | Time (minutes) | % TDI | Time (minutes) | % TDI |
| 2 | 3.52 | 2 | 5.41 | 2 | 6.21 |
| 6 | 4.50 | 6 | 5.94 | 4 | 6.31 |
| 10 | 5.13 | 10 | 6.11 | 6 | 6.29 |
| 15 | 5.49 | 15 | 6.14 | 8 | 6.29 |
| 20 | 5.75 | 20 | 6.20 | 10 | 6.27 |
| 25 | 5.89 | 25 | 6.29 | 15 | 6.28 |

Although the invention has been described in detail in the foregoing for the purpose of illustration, it is to be understood that such detail is solely for that purpose and that variations can be made therein by those skilled in the art without departing from the spirit and scope of the invention, except as it may be limited by the claims.

What is claimed is:

1. A process for recovering toluene diisocyanate (TDI) from a TDI residue solution, comprising
   (a) mixing the TDI residue solution with a polyisocyanate consisting essentially of methylenediphenyl diisocyanate (MDI) or MDI in combination with its higher ring oligomers,
   (b) heating the resulting mixture over a temperature range from 130° to 250° C. at reduced pressure for a period of time sufficient to remove free TDI,
   (c) recovering free TDI removed in (b),
   (d) maintaining or increasing the temperature of the mixture of (b) for a period of time sufficient for equilibration of the TDI residue and MDI and any MDI oligomer to occur, and
   (e) recovering TDI which is thermally split during (d) by either a batch or continuous process.

2. The process of claim 1, wherein steps (b), (c), (d) and (e) are carried out over a temperature range of from 130° to 250° C. over a period of 1 to 180 minutes.

3. The process of claim 2 in which step (d) is conducted at a temperature of from 160° to 220° C. over a period of from 2 to 120 minutes.

4. The process of claim 3 wherein step (d) is conducted at a temperature of from 190° to 210° C. over a period of from 3 to 90 minutes.

5. A continuous process for removing TDI monomer from a TDI residue solution comprising mixing the TDI residue solution with MDI or MDI with its higher ring oligomer, followed by removing free TDI monomer present in the TDI residue solution by passing the resulting mixture through an evaporation means at a reduced pressure, followed by heating at 160° to 250° C. for between 1 and 30 minutes, followed by again passing the mixture through an evaporation means at a reduced pressure to remove TDI monomer generated by the equilibration of TDI residue with MDI or the MDI oligomer, followed by optionally repeating the equilibration-evaporation steps at a reduced pressure until no thermally splittable TDI remains.

* * * * *